United States Patent
Vial et al.

(10) Patent No.: US 11,562,823 B2
(45) Date of Patent: Jan. 24, 2023

(54) METHOD AND SYSTEM FOR REMOTE MONITORING OF A SOFTWARE MEDICAL DEVICE

(71) Applicant: VOLUNTIS, Paris (FR)

(72) Inventors: Etienne Vial, Levallois Perret (FR); Romain Marmot, Suresnes (FR)

(73) Assignee: VOLUNTIS, Paris (FR)

( * ) Notice: Subject to any disclaimer, the term of this patent is extended or adjusted under 35 U.S.C. 154(b) by 1051 days.

(21) Appl. No.: 14/766,138

(22) PCT Filed: Feb. 17, 2014

(86) PCT No.: PCT/FR2014/050321
§ 371 (c)(1),
(2) Date: Aug. 6, 2015

(87) PCT Pub. No.: WO2014/125235
PCT Pub. Date: Aug. 21, 2014

(65) Prior Publication Data
US 2015/0370983 A1    Dec. 24, 2015

(30) Foreign Application Priority Data
Feb. 15, 2013   (FR) ...................... 13 51333

(51) Int. Cl.
*G16H 40/63* (2018.01)
*G16H 40/40* (2018.01)
*G16H 40/67* (2018.01)

(52) U.S. Cl.
CPC ............. *G16H 40/63* (2018.01); *G16H 40/40* (2018.01); *G16H 40/67* (2018.01)

(58) Field of Classification Search
CPC ........ G16H 40/40; G16H 40/63; G16H 40/67; G06F 19/3418; G06F 19/3406
See application file for complete search history.

(56) References Cited

U.S. PATENT DOCUMENTS 7,389,144 B1 *   6/2008  Osorio .................... A61B 5/01
                                                        607/29
2002/0082665 A1 *   6/2002  Haller ................ A61N 1/37264
                                                        607/60
(Continued)

FOREIGN PATENT DOCUMENTS

WO    2009/137699 A2    11/2009
WO    WO-2012138983 A1 * 10/2012    .......... G06F 11/0715

OTHER PUBLICATIONS

Murphy, Lock Up Your Software, Dec. 2000, Embedded Systems Programming, pp. 93-96. (Year: 2000).*

(Continued)

*Primary Examiner* — Christopher L Gilligan
(74) *Attorney, Agent, or Firm* — Nixon & Vanderhye

(57) ABSTRACT

A method for monitoring a medical device (DM) available to a patient (P), the medical device (DM) including a communication terminal (T) implementing software functionalities (f1, f2, f3) for accompanying the patient (P) in a predetermined therapeutic treatment, the method including: —a step (S1) of receiving the current data (DC) on execution of the software functionalities (f1, f2, f3) coming from the medical device (DM), —a step (S2) of testing the current data (DC) by comparison with reference data (DR) according to at least one predetermined vigilance rule (R) associated with a risk for the patient, and —a step (S3) of sending a vigilance message (M1) when such a risk is identified.

13 Claims, 2 Drawing Sheets

(56) References Cited

U.S. PATENT DOCUMENTS

Figure 1:
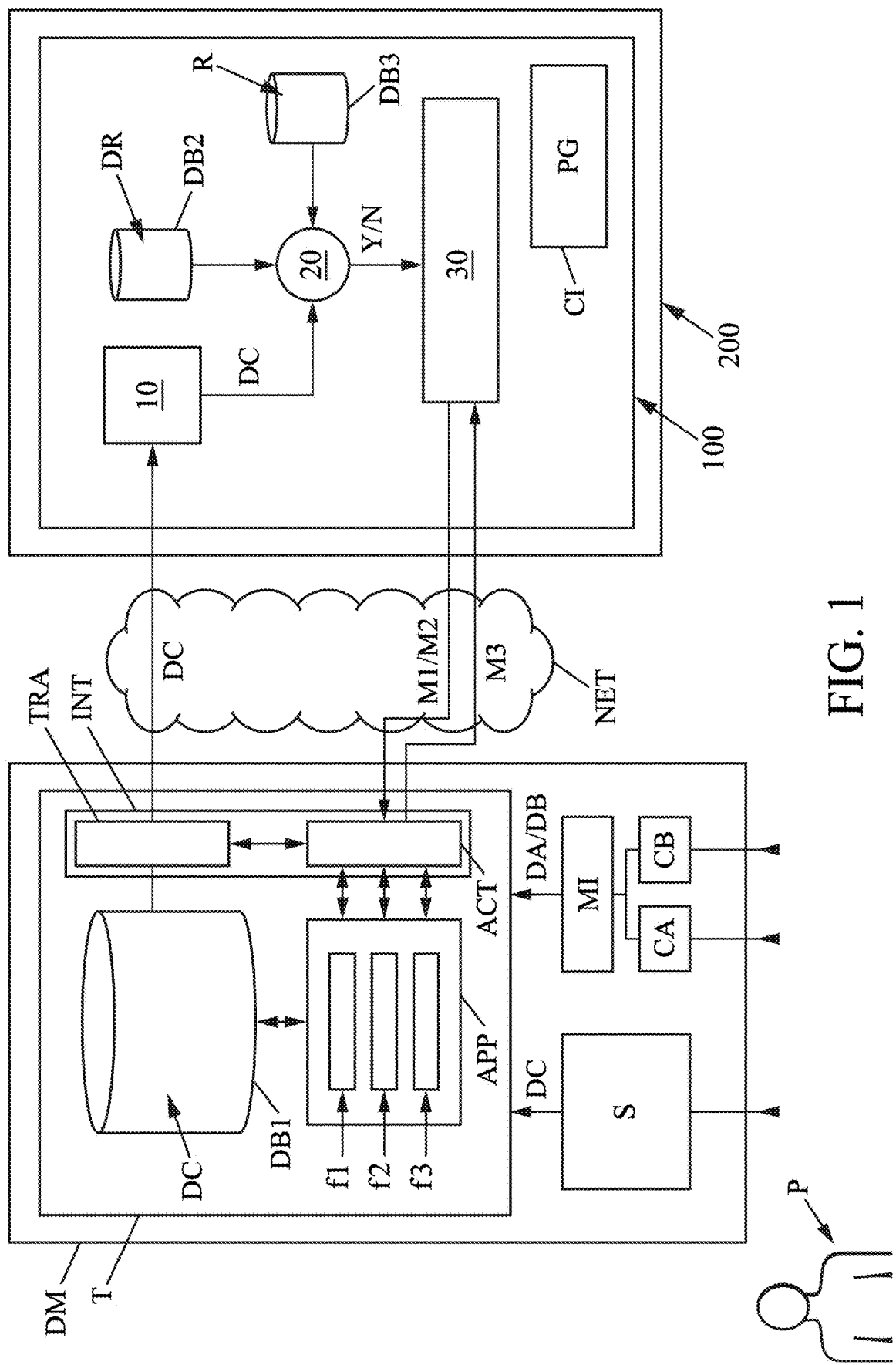

| | | | | |
|---|---|---|---|---|
| 2002/0161990 A1* | 10/2002 | Zhang | ............... | G06F 8/61 |
| | | | | 713/1 |
| 2003/0095648 A1* | 5/2003 | Kaib | ............. | A61B 5/0006 |
| | | | | 379/106.02 |
| 2009/0055938 A1* | 2/2009 | Samuel | ............. | G06F 21/10 |
| | | | | 726/30 |
| 2009/0282244 A1 | 11/2009 | Brown | | |
| 2011/0320595 A1 | 12/2011 | Konishi et al. | | |
| 2012/0172687 A1* | 7/2012 | Wood | ............... | G06F 8/60 |
| | | | | 600/323 |
| 2013/0167250 A1* | 6/2013 | Balasubramanian | ... | G06F 21/31 |
| | | | | 726/28 |
| 2013/0247194 A1* | 9/2013 | Jha | ................ | H04L 63/1425 |
| | | | | 726/23 |

OTHER PUBLICATIONS

International Search Report, dated Jul. 2, 2014, from corresponding PCT application.

Hegde et al., "Case Study—Post Market Product Monitoring System," Reliability and Maintainability Symposium (RAMS), 2011 Proceedings—Annual, IEEE, Jan. 24, 2011, pp. 1-5.

\* cited by examiner

METHOD AND SYSTEM FOR REMOTE MONITORING OF A SOFTWARE MEDICAL DEVICE

TECHNICAL FIELD AND PRIOR ART

The subject matter of the present invention deals with the field of medical devices and relates more particularly to so-called software medical devices.

Software can now be considered to be a medical device provided that it is intended by the manufacturer to be used specifically for diagnostic and/or therapeutic purposes in particular.

Software as a medical device may therefore have a direct influence on the health of the patient. Consequently such software is liable to represent a risk for the patient if one of its functionalities is faulty.

Let us take the simple example of an asthmatic patient: the use of a software medical device intended to accompany the patient in the treatment of the asthma may make it possible to determine the recommended dose of a bronchodilator in order to avoid or limit the asthma attacks; this may be done for example according in particular to:

information relating to the peak expiratory flow (PEF) measured by means of a suitable measuring appliance, and a medical prescription drawn by a specialist doctor taking into consideration information relating to the patient (for example, type of asthma, age, weight, regular activity of the patient, antecedent, etc.).

It will be understood here that this dosing of the bronchodilator must be in accordance with the medical prescription and the state of health of the patient; an error in determining this dose due for example to a computer bug, incompatibility of the software version with its computer environment or an error in the PEF measured may have consequences for the health of the patient, such an error in the dosing being able in some extreme cases to lead to the death of the patient.

Obviously treatment of asthma is one example among other examples: it is in fact possible to provide a software medical device for accompanying the patient in the treatment of other types of pathologies such as for example the treatment of cardiovascular disorders, multiple sclerosis (MS) or epilepsy.

In order to limit the risks related to the use of a software medical device, it is essential for the latter to be used under the conditions and for the purposes provided for by the manufacturer; this makes it possible not to compromise the clinical state or safety of the patient.

However, despite the various national, EC and international regulations, and the quality procedures established at manufacturers for limiting the risks, it is very difficult or even impossible to reproduce, before marketing, all the situations with which the medical device may be confronted.

There therefore exist procedures for monitoring medical devices after marketing thereof in order to limit these risks, or at the very least to take the necessary steps when a potential risk or an incident has been identified.

"Medical device vigilance" is spoken of.

This "medical device vigilance" is generally orchestrated by the health authorities in order to collect and analyse incidents of risk, which have occurred or risk occurring, with medical devices already put on the market.

In the specific case of a software medical device, this "medical device vigilance" involves monitoring all the risks related to the failure or misuse of one of the functionalities offered by the software.

Computer solutions are in fact, by nature, subject to abnormalities and computer bugs, which are often difficult to detect.

This involves the systematic identification of any computing or hardware problem related to the software medical device: computer or software incompatibility, erroneous upgrading, obsolete operating system, desynchronised clock, interoperability problem, ancillary equipment model (for example a measuring appliance or a sensor) that is not supported, etc.

Once the problem has been identified, it is studied in accordance with the quality procedure standardised and supervised by the competent authorities. During these studies, the risks incurred by the patient are evaluated.

At the end of these studies, the competent authorities may or may not require the triggering of a corrective action procedure (known by the term "field safety corrective action") or return procedure (known by the term "medical device recall").

The document US 2009/0282244 attempts to provide a solution to this problem of "medical equipment vigilance" and proposes, with each medical device, the distribution of an authentication key.

The technology deployed in this document requires the sending of this key to a computer server before each use. For its part, the server manages a pre-established list of keys from which access is authorised. Once the authorisation has been delivered by the server after verification of the key on the list, the patient can freely use his medical device.

The solution proposed here is particularly cumbersome to manage on a computer level, both with regard to the server and with regard to the user himself.

Moreover, such a solution requires a permanent access to the network, which is constraining in particular for a patient who is travelling abroad or is in an area not covered by the network.

The applicant submits that the authentication by key proposed in this document allows effective use of the medical device by activating all the software functions of said medical device. However, with the technology proposed in this document, when the authentication fails the medical device overall is deactivated; such an approach is not acceptable in situations where some of the software functionalities would be vital for the patient.

The document WO 2009/137699 proposes a solution substantially identical to the one proposed in the document US 2009/0282244. More particularly, in this document, so-called safety information associated with a kit is recorded on a medium and enables a controller to authenticate the origin of the medical treatment kit.

In this document, the authentication aims simply to verify that the kit intended to be used here is compatible with the medical device. If the authentication is positive, the controller authorises the delivery of the kit treatment by the medical device.

This solution makes it possible to check the matching of the kit with the medical device, the safety information here fulfilling the role of an authentication key.

The approach proposed in this document is therefore advantageous when the computer environment of the medical device does not change, which is generally the case with conventional medical devices. This is because the computer and software environment of a conventional medical device does not change since this environment forms an integral part of the device.

Contrary to this, the computer and software environment of a software medical device is non-stable and non-controlled. A software medical device within the meaning of the present invention may in fact undergo numerous computer and software changes such as for example upgrades, a new software version, etc.

This is all the more true when the software medical devices are distributed and integrated on terminals intended for the general public, such as Smartphones or tablets, such terminals not being dedicated initially to medical use.

The applicant submits that the solutions proposed in the document WO 2009/137699 and in the document US 2009/0282244 cannot take into consideration changes in the computer hardware environment of a software medical device.

As explained previously, this continuous taking into consideration of the changes in the computer and hardware environment of a medical device is a new constraint that appears with the emergence of software medical devices; such a constraint cannot be ignored since the health of the patient may depend on these changes; this is because, as explained above, all these changes may have a negative influence on the correct functioning of one or other of the functionalities proposed by the software.

In any event, neither of these two documents makes it possible to continuously control the operating capabilities of a software functionality of a software medical device and to sound out any uncontrolled changes to the extrinsic data of said device.

The applicant thus submits that the document WO 2009/137699 does not allow systematic identification of a computer or hardware problem related to the software medical device such as for example computer or software incompatibility, erroneous upgrading, obsolete operating system, desynchronised clock, interoperability problem, auxiliary equipment model not supported, etc.

This is because, as indicated above, the approach proposed in this document WO 2009/137699 does not make it possible to verify that the kit intended to be used here is compatible with the medical device.

There therefore does not exist at the present time any effective and efficient technical solution for effectively monitoring software medical devices.

The recent status of software as a separate medical device therefore requires new constraints with which all actors in the health field must deal.

SUMMARY AND SUBJECT MATTER OF THE PRESENT INVENTION

The present invention aims to improve the current situation by proposing a solution taking into consideration the emergence of software medical devices in the health system and remedying the drawbacks of the prior art mentioned below.

One of the objectives of the present invention is to allow the monitoring of a software medical device in order to avoid in particular incidents or risks of incidents involving one or more functionalities of the software occurring (or being reproduced).

The present invention also aims to allow optimum management of the recall or corrective action procedures for software medical devices.

To this end, the subject matter of the present invention relates to a monitoring method that is implemented by computer means and which allows the monitoring of one or more medical devices available respectively to one or more patients.

According to the present invention, the medical device comprises a communication terminal that uses software functionalities to accompany the patient in a predetermined therapeutic treatment.

These are functionalities allowing for example: the dosing of a bronchodilator for treating asthma, monitoring the observance of the treatment against certain autoimmune illnesses, dosing of an anticoagulant for the treatment of certain heart problems, dosing of carbamazepine for treating epilepsy, etc.

Obviously these examples of functionalities under no circumstances have a limitative character; these examples are purely illustrative and a person skilled in the art will understand here that other functionalities coming for example within the medical device field may be envisaged in the scope of the present invention for accompanying a patient in the treatment of other pathologies.

According to the present invention, the monitoring method comprises a step of receiving current data on the execution of software functionalities, these current data coming from the medical device.

Preferably, these current data are transmitted proactively by the medical device when for example the patient operates the medical device.

The current data correspond here to data containing at least one item of information relating to the state in particular of:

the communication terminal itself (for example the model number of the terminal, its operating system, its internal clock, etc.), and/or the software application that supports the various software functionalities (for example the version of the software application, its last upgrades, etc.), and/or the patient (his age, his gender, his activity, his country, the pathology to be treated, etc.).

These current data are intended to be executed and/or used by the software functionalities of the medical device.

Collecting these current data is characteristic of the present invention for the following treatment.

This is because the monitoring method according to the present invention comprises a test step that consists of comparing these current data with reference data. This comparison is done according to at least one predetermined vigilance rule that is associated with a risk for the patient. It will be understood here that the risk is related to the execution of at least one of the software functionalities with the current data. Advantageously, each vigilance rule is related to an identified risk in the execution of at least one of the functionalities of the medical device with the current data. This vigilance rule was established upstream of the method when for example a risk was identified or an incident was reported.

This test makes it possible to identify a risk when the current data do not satisfy the conditions defined by the vigilance rule: a risk is identified when for example the result of the comparison between the current data and the reference data results in an expected value or a value that is higher than a predetermined tolerance threshold.

The applicant submits here that no document of the prior art provides a comparison test based on at least one vigilance rule.

Obviously it is necessary to understand here that a person skilled in the art, in implementing the step, will have the choice of implementing several types of test to compare the current data with reference data and to identify a risk according to this comparison and a predetermined vigilance rule. This comparison may for example, on a mathematical level, be the calculation of a difference, of an absolute value of a difference, of a ratio, etc.

The result of this comparison, which, by virtue of the vigilance rule, results in the identification or not of a risk, makes it possible to follow suitable action: to this end, the monitoring method according to the present invention comprises a sending step during which a vigilance message is sent when a risk is identified; this is particularly advantageous in comparison with the solutions of the prior art (in particular in document WO 2009/137699) in which the medical device is routinely deactivated if the authentication key results in a negative comparison test.

Thus, by virtue of this succession of technical steps, a feature of the present invention, the monitoring method makes it possible to connect information relating to the intrinsic and/or extrinsic state of the medical device (the state of the communication terminal, of the software application, and/or of the patient) and to compare this information with expected reference data. This comparison makes it possible, according to at least one predetermined vigilance rule, to identify the presence or not of a potential risk, such a risk being related to at least one of the functionalities of the software medical device.

The applicant observes that at least one vigilance rule is determined for each potential risk.

In other words, the test made according to the present invention makes it possible to identify a potential risk for the patient in the execution of one or more functionalities of the software medical device with the current data, this risk being due for example to computer incompatibility between the software version and the computer environment offered by the communication terminal.

Preferably, when such a risk is identified, the vigilance message is sent to the medical device, in particular to warn the patient.

This vigilance message may also be sent to the treating doctor and/or the person responsible for the medical monitoring of the patient and/or for the observance of the treatment (for example a nurse).

Advantageously, the vigilance message comprises an order for deactivating remotely the software functionality or functionalities when such a risk is identified.

This therefore makes it possible to remotely deactivate the functionality or functionalities that are giving rise to the risk, this risk being directly related to the execution of this or these functionalities with the current data.

This embodiment is particularly suited to targeting medical devices that present a risk for the patient because for example of a software failure. Such an embodiment makes it possible to avoid return campaigns, which are expensive, lengthy and tedious to implement, and which are normally launched on all devices when this type of risk is identified.

This deactivation of at least one software functionality can be done until a correction is made to said functionality: a computer upgrade for example.

This partial deactivation of the functionality or functionalities to which the potential of risk relates affords a veritable precision that is not found in the prior art.

Advantageously, when no risk is identified, a validation message is sent; this validation message includes an instruction to keep the software functionalities active. Such a validation method guarantees that the active functionalities cannot give rise to any risk (already known and listed). This reinforces the safety of the patient in the use of the medical device.

Preferably, the software functionalities of the medical device are deactivated by default (during a first use following an upgrade for example). In this variant, the validation method therefore allows activation of these functionalities for their first use.

Preferably, the validation message comprises an instruction for keeping the software functionalities active during a predetermined period of validity.

In this variant, it can be envisaged providing that the medical device comprises specific computing means for automatically deactivating the corresponding functionality or functionalities when this period of validity has been passed. This vigilance mechanism, internal to the medical device, limits the risks, for example when the patient is no longer connected to the network.

This vigilance mechanism uses for example an internal clock.

In an advantageous embodiment, the vigilance rule comprises a criterion of compatibility of the software functionalities with a software and/or hardware environment.

This embodiment makes it possible to check that the software functionalities that are implemented on the medical device function correctly with the software and/or hardware environment of the medical device. Incompatibility between these functionalities and the software and/or hardware environment of the medical device could in fact give rise to a computer bug or a failure in the execution of at least one of the software functionalities: for example, an error in calculating the dosage of the bronchodilator.

This embodiment therefore makes it possible to identify the potential risks related to such an incompatibility, and where applicable to deactivate the corresponding functionality or functionalities if the potential risk is judged to be high by the competent authorities.

In another advantageous embodiment, which may optionally be combined with the previous embodiment, the current data contain at least one item of information relating to a version of the software functionalities.

The software functionalities may in fact undergo regular upgrades. In this case, it is possible that a software upgrade is not compatible with the software and/or hardware environment of the medical device: for example, the environment is obsolete and does not support the new version of the software. In this embodiment, the information relating to a version of the software functionalities is therefore verified in order to identify potential risk and, where applicable, it is indicated to the patient in the validation message that an upgrade is necessary in order to correctly use the medical device.

In another advantageous embodiment, which may optionally be combined with one or other or both of the previous two embodiments, the current data comprise information on the computer environment version for executing the software functionalities.

In this case, this information is compared with the information relating to the computer environment of the medical device.

In another advantageous embodiment, which may optionally be combined with one or other or both of the previous three embodiments, the current data comprise communication terminal model information.

In this case, it will be understood that the test may consist for example of comparing this information with the information relating to the communication terminal models that are considered to be able to support the software functionalities. If the communication terminal model of the medical device does not form part of this list (it is here the vigilance rule that is established), then a potential risk is identified: this risk identified here is related directly to the use of this terminal model.

Preferably, the medical device comprises, apart from the communication terminal, an auxiliary medical measurement device such as for example a sensor for measuring the PEF of the patient or a cardiac sensor for measuring the heart rate of the patient, or his blood pressure.

In this variant, the current data comprise model information for this auxiliary device. It will be understood here that the vigilance rule comprises a criterion on compatibility between the auxiliary device and the medical device. The comparison established during the test step consists in this case of comparing this information with the reference data relating to the various models expected, taking this compatibility criterion into consideration. If the model of the auxiliary device is not compatible with the medical device, this may mean that there exists a risk that the measurements made by the auxiliary device are not reliable; in this case, deactivation of the "measurement of the auxiliary measurement device" functionality is required.

The medical device preferably comprises:
at least one sensor for the activity of the patient, and
a module for interpreting this activity in order to determine an activity data item for the patient.

In this variant, the current data comprise this activity data item for the patient.

In the same way, the medical device can also comprise at least one so-called biological sensor for measuring a biological signal relating to the patient, such a signal comprising biological information relating to the biological state of the patient. In this variant, the interpretation module is configured so as to determine a biological data item for the patient.

In this variant, the current data comprise this biological data item for the patient.

Correspondingly, the subject matter of the present invention relates to a computer program that contains instructions suitable for executing steps of the monitoring method as described above, in particular when said computer program is executed by at least one processor.

Such a computer program may use any programming language and be in the form of a source code, an object code or a code intermediate between a source code and object code, such as in a partially compiled form, or in any other desirable form.

Likewise, the subject matter of the present invention relates to a recording medium that can be read by a computer, on which a computer program is recorded, comprising instructions for executing steps of the monitoring method as described above.

Firstly, the recording medium may be any entity or device capable of storing the program. For example, the medium may comprise a storage means, such as a ROM memory, for example a CD-ROM or a ROM memory of the microelectronic circuit type, or a magnetic recording means, for example a diskette of the floppy disk type or a hard disk.

Secondly, this recording medium may also be a transmissible medium such as an electrical or optical signal, such a signal being able to be routed via an electrical or optical cable, by conventional or wireless radio or by auto-directed laser beam or by other means. The computer program according to the invention may in particular be downloaded on a network of the Internet type.

Alternatively, the recording medium may be an integrated circuit in which the computer program is incorporated, the integrated circuit being suitable for executing or being used in the execution of the method in question.

The subject matter of the present invention also relates to a system for monitoring a medical device available to a patient, said medical device comprising a communication terminal implementing software functionalities for accompanying the patient in a predetermined therapeutic treatment.

According to the present invention, the monitoring system comprises:
a receiver that is configured so as to receive from the medical device current data on execution of the software functionalities;
a test circuit that is configured so as to compare the current data with reference data according to at least one predetermined vigilance rule associated with a risk for the patient, this risk being related to the execution of the at least one of the software functionalities with the current data, and
a transmitter that is configured so as to send a vigilance message when such a risk is identified.

Advantageously, the monitoring system comprises computer means that are configured so as to enable the various steps of the monitoring method as described above to be implemented.

The subject matter of the invention also relates to a computer server for monitoring a medical device made available to a patient, said computer server comprising a monitoring system as described above.

The subject matter of the present invention also relates to a medical device available to a patient; this medical device is configured so as to enable the monitoring method to be implemented by the monitoring system described above.

According to the present invention, the medical device comprises:
a communication terminal that implements software functionalities for accompanying the patient in a predetermined therapeutic treatment,
a transmission means that is configured to transmit current data on execution of said software functionalities intended for a monitoring system as described above, and
a vigilance means that is configured so as to deactivate at least one software functionality on reception of a vigilance message sent when a risk has been identified by the monitoring system, said vigilance message comprising an instruction for deactivating said at least one software functionality.

Advantageously, the transmission means is configured to transmit the current data periodically (that is to say according to a given periodicity, for example every hour, every day, every week, etc.).

Advantageously, the monitoring system is configured to send a validation message when no risk has been identified. In this case, in a preferred variant, the vigilance means is configured so as to deactivate at least one of the software functionalities of the medical device when no validation message coming from the monitoring system has been received.

Optionally, the validation message comprises an instruction for keeping the software functionality or functionalities active during a predetermined period of validity. In an advantageous variant, when no validation message coming from the monitoring system has been received during a period greater than the period of validity, then the vigilance means is configured to deactivate at least one of the software functionalities.

The medical device may also comprise an internal clock for deactivating the functionality or functionalities when the period of validity has expired or when no validation message has been received for a predetermined period.

Thus the subject matter of the present invention, through its various functional and structural aspects described above, enables at least one software medical device to be monitored remotely in order in particular:

to warn the patient of a potential risk related to the use of the software medical device and in particular a risk related to the execution of at least one of the software functionalities of this software medical device, and to manage optimally the corrective actions and/or the return actions related to said devices when such a risk is identified.

BRIEF DESCRIPTION OF THE ACCOMPANYING FIGURES

Figure 2:
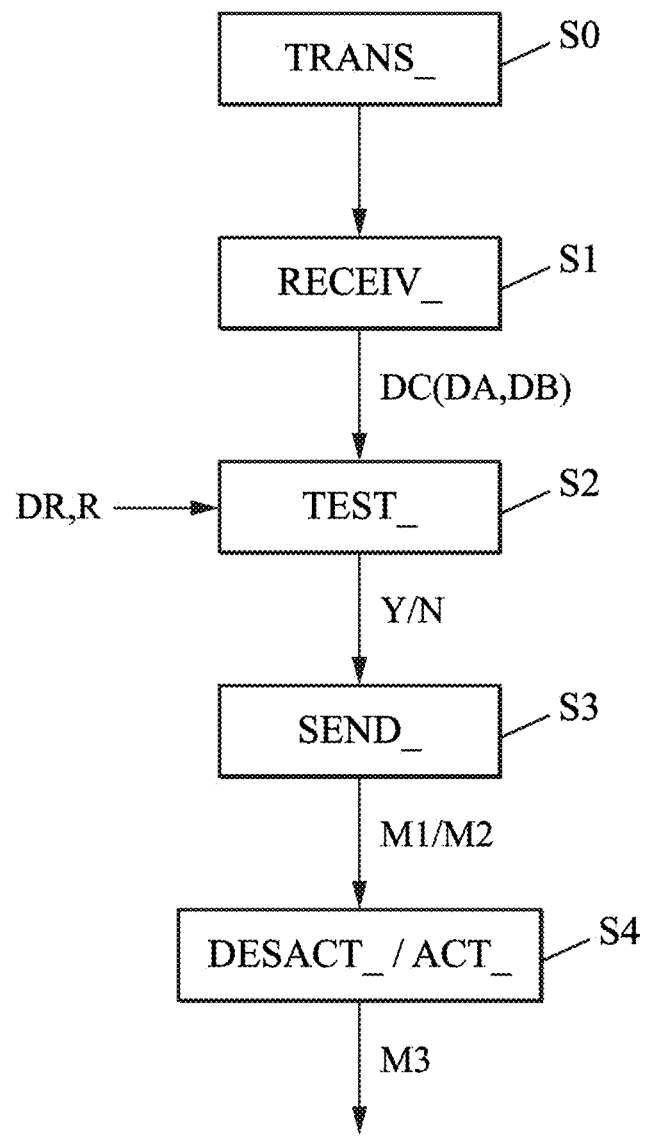

Other features and advantages of the present invention will emerge from the following description with reference to the accompanying FIGS. 1 and 2, which illustrate an example embodiment thereof devoid of any limitative character and in which:

FIG. 1 depicts schematically a computer server comprising a system for the remote monitoring of at least one software medical device according to an example embodiment of the present invention; and FIG. 2 depicts a flow diagram illustrating the monitoring method according to an example embodiment of the present invention.

DETAILED DESCRIPTION OF VARIOUS ADVANTAGEOUS EMBODIMENTS

A method for monitoring a software medical device DM and the monitoring computer system 100 that is associated therewith will now be described hereinafter with reference conjointly to FIGS. 1 and 2.

Enabling one or more software medical devices DM to be monitored in a "medical device vigilance" problem is one of the objectives of the present invention.

In the example described here, the software medical device DM in question is configured for accompanying a patient P suffering from arterial hypertension.

In this example, in order to treat this pathology, the patient P must take a medication of the conversion enzyme inhibiter type, hereinafter denoted CEI. This medication requires regular adaptation of the dosage, which depends in particular on the systolic blood pressure of the patient P.

Obviously, as explained above, this example is purely illustrative and under no circumstances has a limitative character: a person skilled in the art will understand here that the patient P may be accompanied in the treatment of any other type of pathology using a medical device DM within the meaning of the present invention: the example described here may thus be transposed without any difficulty to the treatment of another pathology such as for example asthma, MS, etc.

In the example described here and as illustrated in FIG. 1, the software medical device DM therefore comprises a communication terminal T such as for example a Smartphone or a digital tablet on which a software application APP is integrated, supporting several functionalities f1, f2 and f3 for accompanying the patient P in his treatment.

In the example described here, there is, among the functionalities f1, f2 and f3, the functionality f1 that relates to an algorithm relating to the calculation of the dosage of the CEI. This algorithm, in calculating the CEI dosage, takes into consideration in particular the variations in the hypertension of the patient P.

In the example described here and as illustrated in FIG. 1, the medical device DM comprises an auxiliary device such as a cardiac sensor S especially configured to measure the systolic blood pressure of the patient P and to identify the variations in hypertension. This sensor S consists for example of a pressure auto-measurement apparatus.

It is considered that in the example described here this sensor S bears the model number "X-1".

In the example described here, each day before taking his treatment dose, the patient P measures his pressure by means of this sensor S in order to know the dose of CEI that he must take.

In the case of a patient suffering from hypertension, it is generally expected that this measurement will be between 10 and 20 centimetres of mercury (cm Hg).

In a first example embodiment described here and to illustrate one of the numerous advantages of the present invention, the patient P must change the batteries of the sensor S that are old.

However, this change of batteries here causes the sensor S to be reset to the factory parameters; in the working hypothesis developed here, which is purely illustrative, this hardware problem (resetting to the factory parameters) had not been identified by the manufacturer before putting on the market.

Thus, in this example, following this resetting to the factory parameters, the measurement unit becomes the millimetre of mercury (mm Hg): the values of the pressure measurement are now between 100 and 200 (mm Hg) instead of the 10 to 20 (cm Hg) expected.

Following this change of batteries, the patient P makes his measurement and enters in the application APP the value that he reads on the sensor S, namely for example the value 140 (this entry of the value measured can be done automatically).

In the example described here, having regard to this value (which is ten times higher than the expected value), the algorithm relating to the dosage functionality f1 recommends for the patient P a dose of CEI that is appreciably higher than the required dose: this change of batteries in the sensor S therefore here gives rise to a manifest error in dosage.

Following this taking, the patient P falls ill and is hospitalised.

In this case, a "medical device vigilance" incident is reported immediately to the competent health authorities, for example through the treating doctor, who fills in a suitable form according to the conventional standard procedure.

In the example described here, a study of the incident then reveals that there exists a failure in the mechanism for checking the blood pressure entry field, the upper limit of which was poorly defined.

To remedy this problem of computer parameterising, it is necessary to proceed with a correction to the algorithm f1 (by a software upgrade) in order to modify this upper limit and add a limit not to be exceeded for the dose recommended by the medical device DM.

In this example, the time necessary for the specification, development, checking and validation of the upgrade to this functionality f1 is estimated at several weeks.

Because of the criticality of the incidents encountered, in consultation with the public authorities, action is necessary urgently with all the patients P suffering from hypertension and using medical devices DM functioning with the auxiliary device S corresponding to the model "X-1". This is because, for these devices DM, it is necessary to deactivate the functionality f1 as quickly as possible until a correction is made.

As illustrated in FIG. 1, the present invention for this purpose provides a computer server 200 that comprises a monitoring system 100 for monitoring the medical devices DM and having computer means for carrying out vigilance action.

In the example described here, and as illustrated in FIGS. 1 and 2, the medical device DM comprises an interface module INT that can communicate with the monitoring system 100 according to the present invention.

As illustrated in FIGS. 1 and 2, this interface module INT has a transmission means TRA that is configured so as to proactively transmit, during a transmission step S0 via the network NET, data such as current data DC that are particular to the device DM and are stored on each device DM in a first database DB1.

In the example described here, the current data DC contain the information relating to the model number of the sensor S.

These transmission means TRA are deployed on all medical devices DM making it possible to collect the current data DC of each device DM.

The monitoring system 100 for its part comprises a receiver 10 for receiving these data DC during a reception step S1.

Making it possible to identify the medical devices DM functioning with a sensor S of the "X-1" type is here the objective sought.

In the example described here, and as illustrated in FIGS. 1 and 2, the monitoring system 100 comprises a test circuit 20 that is configured to test, during a test step S2, the current data DC collected for each medical device DM, comparing them with reference data DR according to a vigilance rule R.

In the example described here, the reference data DR are stored on a second database DB2.

In this example, the reference data DR may correspond to the data relating to the model number of the sensor S; the vigilance rule R, which was defined by the administrator of the server 200 (in accordance with the recommendations of the health authorities) and is stored on a third database DB3 therefore makes it possible, by virtue of the comparison between the current data DC and the reference data DR, to identify all the devices DM comprising a sensor of the "X-1" type.

The system 100 comprises computer means especially suitable for configuring the vigilance rules R that it is necessary to execute in order to identify the devices DM at risk (not shown here).

In the example described here, the vigilance rule R therefore comprises an incompatibility criterion for the sensor S of type "X-1" with the functionality f1. The comparison between the current data DC and the reference data DR correlated with this vigilance rule R thus makes it possible to target the devices DM comprising this sensor S of type "X-1" and to which this problem relates.

This comparison test is characteristic of the present invention: it makes it possible to effectively make a distinction, of the "yes or no" (y/n) type in order to identify the devices DM presenting a risk.

In the example described here, and as illustrated in FIGS. 1 and 2, the system 100 comprises a transmitter 30 that is configured so as to send, during a transmission step S3, a vigilance message M1 to each medical device DM identified as comprising a sensor S of the "X-1" type.

In the example described here, the vigilance message M1 is sent (for example by "push" message) in order to warn the patients P having a sensor S of the "X-1" type of the potential risks related to the functionality f1.

In the example described here, the vigilance message M1 is further programmed to enable this function f1 relating to the dosage of the CEI to be deactivated.

In the example described here and as illustrated in FIG. 1, the interface module INT of the medical device DM comprises a vigilance means ACT configured to receive the vigilance message M1 and carry out the necessary actions according to the instructions contained in this message M1: for example here deactivate the functionality f1, during a deactivation step S4.

This vigilance module ACT can also send to the server 200 a confirmation message M3 to indicate to the system 100 that deactivation of the functionality f1 has been correctly executed.

It is also possible to provide for the sending of a warning message to warn the treating doctor monitoring the patient P using the medical device DM implementing this functionality f1 (not shown here).

Thus, in this example, by virtue of the present invention, once a risk has been identified (here a dosage problem according to the functionality f1 following a change of batteries for the sensor model "X-1"), it is possible to intervene at a distance and in a very precise fashion, through the network NET, in order to modify the status of the functionality f1 allowing the dosage of CEI and to make it inactive, during a deactivation step S4, for all the medical devices DM integrating the model of sensor S of the "X-1" type.

For devices DM not comprising a model of sensor S of the "X-1" type, no potential risk related to the sensor is identified. In this case, a validation message M2 is sent, during the sending step S3, to these devices. This message M2 may contain an instruction for keeping the functionality f1 active.

As illustrated in FIG. 1, this monitoring is carried out by executing computer instructions contained in a computer program PG for implementing all the steps of the monitoring method described above. In this example, the program PG is recorded on a computer medium CI such as a microprocessor or an integrated circuit.

A person skilled in the art will understand here that numerous other advantageous example embodiments may also be envisaged in the context of the present invention.

According to another example, it is possible that the error in the dosage of CEI produced by the functionality f1 may have its origin in incompatibility between the model of communication terminal T and the version of the software application APP used.

For example, it is possible that the communication terminal T corresponding to an iPhone5 (registered trade mark) upgraded with an operating system 6.1 or a mobile telephone integrating the "Android" (registered trade mark) operating system in its version 4.2 may not be compatible with the version 1.3 of the application APP for accompanying the patient P suffering from hypertension.

In this example, it may be imagined that version 1.3 of the software application APP and more particularly the functionality f1 relating to the dosage of CEI is faulty with these versions of communication terminal T: this problem of computer incompatibility has for example been identified in advance by a team of computer engineers responsible for "medical device vigilance", following numerous tests following a reported malaise.

In this case, once the incompatibility is identified, a vigilance rule R is defined by the competent authorities and is recorded by the administrator on the third database DB3.

The monitoring system 100 next deploys the method described above for identifying all the medical devices DM comprising an iPhone5 with the operating system 6.1 or a mobile telephone integrating the Android operating system in its version 4.2 and functioning with the version 1.3 of the application APP.

This identification as developed above is made through the reception S1 of the current data DC coming from all the medical devices DM and by comparison S2 of these current data DC with reference data DR expected, these current data DC containing here information relating to the software versions of the application APP and the models of the terminals T.

In making this comparison here, a vigilance rule R comprising the incompatibility criterion defined above and associated with the risk reported in the context of the "medical device vigilance" is taken into consideration. By default, it can be envisaged systematically providing for a vigilance rule R for deactivating all the devices DM that comprise a terminal T with an operating system that has not yet been tested: this avoids the potential risks related to the marketing of a terminal T the operating system of which does not function correctly with the software application.

In this example, once the medical devices DM to which the risk relates have been identified, a vigilance message M1 is sent to each of the devices DM during a sending step S3; this message M1 may indicate to the patient P that an upgrade of version 1.4 of the application APP must be downloaded as quickly as possible.

The vigilance message M1 may also provide for a deactivation of the functionality f1 as long as this version 1.4 has not been downloaded.

Preferably, the vigilance means ACT may comprise an internal clock that calculates the time elapsed following the reception of this message M1. At the end of a given time (24 hours for example), the vigilance means ACT may decide proactively to deactivate the functionality f1 that is posing a problem.

Alternatively, the vigilance means ACT may send a confirmation message M3 when the upgrade has been correctly installed.

In this example, it is also possible to provide for the sending of a validation message M2 when no risk is identified. This validation message M2 comprises for example an instruction to keep the software functionalities f1, f2 and/or f3 of the application APP active, during a given period of validity. This validation message M2 occurs for example when the test reveals that the software version is up to date.

In this case, the internal clock makes it possible to deactivate the software functionality or functionalities f1, f2 and/or f3 of the application APP if the period of time measured from the reception of the last validation message M2 received is longer than the validity period.

In the example described here, provision is also made for the functionalities f1, f2, f3 to be by default parameterised initially in the "deactivated" state. In this case, it is therefore indeed the validation message M2 that makes it possible to activate each of these functionalities, after the monitoring system 100 confirms that no risk is identified.

Such a default configuration avoids the computer problems due to a software upgrade that has not yet been tested.

The medical device DM also comprises computer means especially configured to limit the risks related to at least one of the software functionalities f1, f2 and/or f3.

Thus, advantageously, the transmission means TRA of the medical device TM transmits to the monitoring system 100 the current data DC from the base DB1 according to a given periodicity (for example every day).

Let us take a particular example in which the period of validity of the functionality f1 is one week. If no current data item DC is received by the monitoring system 100 during a period greater than this period of validity (in other words, no validation message M2 is therefore received during this period), then, in this case, the vigilance means ACT deactivates at least one of the functionalities f1, f2 and/or f3, the period of validity of the functionality f1 being expired.

The medical device thus comprises, by virtue of this vigilance means ACT, an internal mechanism that enables it to be automatically warned of the least risk related to the execution of one of the functionalities f1, f2 and/or f3.

This internal mechanism makes it possible in particular to avoid certain risks, in particular when the patient P is situated in an area not covered by the network NET.

Numerous other example embodiments can be envisaged within the scope of the present invention.

Thus, in another example embodiment described here purely by way of illustration, the communication terminal T comprises an activity sensor CA for the patient P, for example a pedometer or a geolocation system.

In this example, the communication terminal T also comprises an interpretation module MI that is configured so as to determine an activity data item DA for the patient, this activity data item DA relating to the activity of the patient P: for example here, this data item DA indicates active walking of the patient for a period of more than one hour.

In this example, the current data DC comprise this activity data item DA.

However, this activity data item DA for the patient P may significantly vary the calculation of the dose of CEI.

In the example described here purely by way of illustration, a situation can be imagined in which it is highly inadvisable to take a dose of CEI following a period of intense physical activity. In this example, the application APP in its current version is defective and does not include this parameter relating to the blocking of the dosage in the case of intense physical activity.

The monitoring system 100 can remedy this defect in the application APP by waiting until a software upgrade is available to the patient P. In this example, the reference data DR expected thus comprise information indicating that the patient P must not do more than one hour of intensive walking. In this case, by deploying the method described above, the test S2, by comparing the current data item DC with the reference data item DR, can make it possible to identify the medical devices DM concerned and to trigger, by sending a vigilance message M1, deactivation of the dosage functionality f1.

Obviously this example is not limited to this precise scenario. It is for example possible to envisage a situation in which the activity data item DA indicates that the patient P is abroad with a time shift of several hours.

Such information may be relevant for example if the patient P must take his dose of CEI at a fixed time. In this case, the monitoring system 100 takes this information into consideration in order to permit or not the activation of the functionality f1, according to the "effective" time for the patient rather than the actual time of the time zone in which he is situated.

This example with the physical activity data item DA of the patient P may also be extended to a more general example in which a biological data item DB or physiological data item of the patient P is used by means of a measurement made directly on the patient P with a sensor CB configured to measure a biological signal relating to the patient P.

Among the many other examples, it is possible to envisage that the medical device DM is deployed on a communication terminal T of the Smartphone type and allows treatment of epilepsy by Carbamazepine.

In this example, a health professional such as the treating doctor enters data relating to the plasma levels associated with a time defined by the internal clock of the terminal T. However, in this example, synchronisation of the clock is deactivated. The data entered are therefore improperly timestamped and are interpreted as prior to the taking of the medication. Faulty timestamping may in this medical context give rise to an erroneous medical decision by the algorithmic system APP embedded in the medical device DM: this may for example cause a wrong dosage according to the functionality f1.

The present invention is configured to allow monitoring of this timestamping and of the internal time of the terminal T (vigilance rule). This is because the system 100 is configured to compare the current time sent by the device DM and forming part of the current data DC and the time of the server 200 forming part of the referenced data DR (the latter being synchronised with a reliable time server).

This comparison during the test step S2 results in the detection of a synchronisation problem and identifies the presence of a potential risk relating to the execution of the functionality f1 relating to the dosage.

The system 100 in this case sends a message to deactivate the functionality f1 for safety reasons.

It will thus be understood, through the various example embodiments described above, that the monitoring system 100 within the meaning of the present invention, which is implemented on a computer server 200, makes it possible to monitor and, where applicable, to deactivate, remotely by means of a network NET and selectively, the software functionality or functionalities f1, f2 and/or f3 of the software application APP implemented on the medical device DM in the various circumstances where a potential risk for the patient is identified and is related to at least one of these functionalities f1, f2 and/or f3.

The present invention thus makes it possible to identify any problem of a software, computing or hardware nature that may give rise to a malfunctioning in the medical device DM, and more precisely in the execution of at least one of the software functionalities f1, f2 and/or f3 of the medical device DM with the current data DC.

This monitoring is done by collecting, during a reception step S1, the current data DC from all the medical devices DM deployed, these current data DC being the execution data that are exploited and/or used by each of the functionalities f1, f2 and/or f3 of each medical device DM.

These current data DC may in particular comprise:
information relating to the communication terminal T that is the host terminal of the medical device DM. It may be a case for example of information relating to the manufacturer, to the make, to the model, to the version, to the operating system, to the version of the operating system, to the identification and version of the components (e.g.: database software, camera, screen resolution, etc.), to an identifier for sending "push" messages. It may also be a case of information relating to the clock of the terminal T: current time, time zone;
information relating to the software application APP supporting the various software functionalities f1, f2 and/or f3: version number, language of use, data of installation, data of activation, configuration;
information relating to the place of use: country, region;
information relating to the network/Internet connection mode: telephone operator, 3G, 4G, Wi-Fi;
information relating to the patient P: identity, age, sex, type of illness, etc.;
information relating to the behaviour, to a biological parameter of the patient or to the activity of the patient P: frequency of use and time of use of certain functionalities, time of switching the terminal T on and off, physical activity, etc.;
information relating to the health professional monitoring the patient P: treating doctor, doctor working in town/hospital/clinic, speciality.

These current data DC are thus compared, during a step S2, by the test circuit 20 of the system 100 with reference data DR stored on a database DB2.

This comparison is next interpreted in accordance with at least one vigilance rule R stored on a database DB3. The treatment of this vigilance rule R and of the result of this comparison makes it possible next to determine whether a potential risk to the patient P is liable to arise during the execution of one of the functionalities f1, f2 and/or f3 with the current data DC.

It will be understood here that the vigilance rules R are to be defined according to each case: these rules R may for example comprise a software, hardware, and/or computer, etc. incompatibility criterion.

These vigilance rules may be implemented and stored on the system 100 by virtue of suitable computer means.

Thus, as developed above, when a risk is identified for a given functionality (for example when a medical device DM functions with a version 1.3 for the application APP and the model iPhone5 functioning with an operating system version 6.1 for the host terminal T), then a vigilance message M1 is sent to all the medical devices DM concerned, during a sending step S3. This message M1 may comprise a simple warning or where applicable may comprise an instruction for deactivating the functionality identified as potentially at risk.

This remote monitoring by a system 100 integrated in a server 200 makes it possible to precisely target the medical devices DM to which an identified potential risk relates. Such a system 100 makes it possible to rationalise return campaigns and issues of corrections, by taking the necessary preventive measures and in particular by temporarily deactivating the functionalities concerned.

One of the other aspects of the present invention relates to computer means (in particular the vigilance means ACT) specific to the medical device DM that enable it, by means of an internal clock mechanism, to warn the medical device DM of any potential risk related to the use of a software functionality, when for example the medical device DM is off connection and does not, for a given period, manage to transmit the current data DC to the monitoring system 100.

It should be observed that this detailed description relates to a particular example embodiment of the present invention but that under no circumstances does this description have any character that is limitative for the subject matter of the invention; quite the contrary, its objective is to remove any possible lack of precision or any faulty interpretation of the following claims.

The invention claimed is:

1. A method for monitoring a medical device that is available to a patient and is equipped with a communication terminal that operates in accordance with software functionalities that accompany the patient in a predetermined therapeutic treatment, said method comprising:

receiving, at a monitoring device, current data from the medical device for executing said software functionalities, said current data being generated by the medical device;

testing said current data at the monitoring device by comparing said current data received from the medical device with reference data according to at least one predetermined vigilance rule associated with a risk for the patient, said risk being related to a malfunctioning of a software functionality when executed with said current data, and thereby determining whether there is a presence of said risk, said software functionality being one among the software functionalities, a determination during the testing of a presence of the risk resulting in automatically sending to said medical device a vigilance message comprising information of said risk determined during the testing together with an instruction that causes deactivation of the malfunctioning software functionality, said deactivation of the malfunctioning software functionality preventing the malfunctioning software functionality from any execution until a corrective event takes place, and a determination during the testing of no presence of the risk resulting in automatically sending a validation message to the medical device, the validation message comprising an instruction that causes the medical device to keep said software functionality active for a predetermined period of validity, wherein said software functionality is automatically deactivated at the medical device upon expiration of said predetermined period of validity if no further validation message is received by the medical device during the predetermined period of validity.

2. The method according to claim 1, wherein the vigilance rule comprises a criterion on compatibility of the software functionalities with a software and/or hardware environment.

3. The method according to claim 1, wherein the current data comprise information relating to a version of the software functionalities.

4. The method according to claim 1, wherein the current data comprise information on the computer environment version executing the software functionalities.

5. The method according to claim 1, wherein the current data comprise information on the model of the communication terminal.

6. The method according to claim 1, wherein the medical device comprises, in addition to the communication terminal, an auxiliary medical measurement device, and the current data comprise information on the model of the auxiliary device.

7. The method according to claim 1, wherein the medical device comprises at least one patient activity sensor and an interpretation module that interprets said activity in order to determine an activity data item on the patient, said current data comprising said activity data item on the patient.

8. A non-transitory computer-readable storage medium having recorded thereon a computer program comprising one or more sequences of instructions executable by a processor of a monitoring device, wherein, upon execution of said computer program by said processor, said program implements a monitoring method for monitoring a medical device available to a patient, said medical device equipped with a communication terminal that operates software functionalities that accompany the patient in a predetermined therapeutic treatment, and wherein said monitoring method comprises:

receiving current data from the medical device for executing said software functionalities, said current data being generated by the medical device, testing said current data received from the medical device by comparing said current data with reference data according to at least one predetermined vigilance rule associated with a risk for the patient, said risk being related to a malfunctioning of a software functionality when executed with said current data, and thereby determining whether there is a presence of said risk, said software functionality being one among the software functionalities, a determination during the testing of a presence of the risk resulting in automatically sending to said medical device a vigilance message comprising information of said risk determined during the testing together with an instruction that causes deactivation of the malfunctioning software functionality, said deactivation of the malfunctioning software functionality preventing the malfunctioning software functionality from any execution until a corrective event takes place, and a determination during the testing of no presence of the risk resulting in automatically sending a validation message to the medical device, the validation message comprising an instruction that causes the medical device to keep said software functionality active for a predetermined period of validity, said software functionality being automatically deactivated at the medical device upon expiration of said predetermined period of validity if no further validation message is sent to the medical device during the predetermined period of validity.

9. A system for monitoring a medical device available to a patient, said medical device comprising:

a communication terminal that operates in accordance with software functionalities that accompany the patient in a predetermined therapeutic treatment, wherein said monitoring system comprises:

a receiver configured to receive from the medical device current data for execution of said software functionalities, a test circuit configured to compare said current data received from the medical device with reference data according to at least one predetermined vigilance rule associated with a risk for the patient, said risk being related to a malfunctioning of a software functionality when executed with said current data, and thereby determine whether there is a presence of said risk, said software functionality being one among the software functionalities, and a transmitter configured to, responsive to a determination during the testing of a presence of the risk, automatically send to said medical device a vigilance message comprising information of the risk determined during the testing together with an instruction that causes deactivation of the malfunctioning software functionality, said deactivation of the malfunctioning software functionality preventing the malfunctioning software functionality from any execution until a corrective event takes place and to, responsive to a determining during the testing of no presence of the risk, send a validation message to the medical device, the validation message comprising an instruction that causes the medical device to keep said software functionality active for a predetermined period of validity, wherein said software functionality is automatically deactivated at the medical device upon expiration of said predetermined period of validity if no further validation message is sent to the medical device during the predetermined period of validity.

10. A computer server that monitors a medical device available to a patient, said computer server comprising a monitoring system according to claim 9.

11. A medical device available to a patient, comprising:
a communication terminal implementing software functionalities that accompanies the patient in a predetermined therapeutic treatment,
a transmitter,
a monitoring system according to claim 9, and
a vigilance safety that automatically deactivates at least one software functionality on reception of a vigilance message sent when a risk has been identified by the monitoring system, said vigilance message comprising an instruction for deactivating said at least one software functionality,
wherein said transmitter automatically transmits current data on execution of said software functionalities to said monitoring system.

12. The medical device according to claim 11, wherein the transmitter transmits the current data periodically.

13. The medical device according to claim 12, wherein the vigilance safety automatically deactivates at least one software functionality when no validation message has been received during a predetermined period.

* * * * *